United States Patent [19]

Kantrowitz et al.

[11] Patent Number: 6,003,174
[45] Date of Patent: Dec. 21, 1999

[54] RADIOLUCENT TABLE EXTENSION AND METHOD

[76] Inventors: Allen Kantrowitz, 5170 Pine Tree Dr.; In Ki Mun, 4045 Sherida Ave., #263, both of Miami Beach, Fla. 33140; Charles E. Dinkler, 524 Hamblin Dr., Cincinnati, Ohio 45255

[21] Appl. No.: 08/922,969

[22] Filed: Sep. 3, 1997

[51] Int. Cl.$^6$ .......................... A61G 13/12; A47G 20/02
[52] U.S. Cl. ............................ 5/601; 5/622; 5/632; 5/638
[58] Field of Search ................. 5/601, 621, 622, 5/632, 638, 640, 643; 248/220.21, 220.22, 224.51

[56] References Cited

U.S. PATENT DOCUMENTS

| | | |
|---|---|---|
| 1,171,713 | 2/1916 | Gilkerson . |
| 2,707,662 | 5/1955 | Goldfield et al. . |
| 2,753,233 | 7/1956 | Rock . |
| 2,840,429 | 6/1958 | McDonald . |
| 2,872,259 | 2/1959 | Thorpe . |
| 3,428,307 | 2/1969 | Hunter et al. . |
| 3,766,384 | 10/1973 | Anderson . |
| 4,076,230 | 2/1978 | Pike . |
| 4,333,638 | 6/1982 | Gillotti ..................................... 5/622 X |
| 4,484,571 | 11/1984 | Velazquez . |
| 4,506,872 | 3/1985 | Westerberg et al. ......................... 5/601 |
| 4,584,731 | 4/1986 | Carter ......................................... 5/632 |
| 4,616,814 | 10/1986 | Harwood-Nash et al. .................. 5/601 |
| 4,669,106 | 5/1987 | Ammerman . |
| 4,688,780 | 8/1987 | Hanz . |
| 4,727,328 | 2/1988 | Carper et al. . |
| 4,881,728 | 11/1989 | Hunter . |
| 4,910,819 | 3/1990 | Brown . |
| 4,914,682 | 4/1990 | Blumenthal . |
| 4,944,501 | 7/1990 | Sireul et al. . |
| 4,989,849 | 2/1991 | Zupancic et al. . |
| 5,088,706 | 2/1992 | Jackson . |
| 5,090,044 | 2/1992 | Kobayashi . |
| 5,155,758 | 10/1992 | Vogl . |
| 5,177,823 | 1/1993 | Riach ....................................... 5/643 X |
| 5,233,713 | 8/1993 | Murphy et al. . |
| 5,276,927 | 1/1994 | Day ......................................... 5/601 X |
| 5,335,384 | 8/1994 | Foster et al. ................................ 5/622 |
| 5,347,668 | 9/1994 | Manning .................................... 5/622 |
| 5,427,436 | 6/1995 | Lloyd . |
| 5,475,884 | 12/1995 | Kirmse et al. . |
| 5,499,415 | 3/1996 | McKenna . |
| 5,560,728 | 10/1996 | McFadden ............................. 5/637 X |
| 5,661,859 | 9/1997 | Schaefer ................................ 5/622 X |
| 5,675,851 | 10/1997 | Feathers . |
| 5,758,374 | 6/1998 | Ronci ..................................... 5/621 X |
| 5,774,916 | 7/1998 | Kurhi ......................................... 5/632 |

FOREIGN PATENT DOCUMENTS

| | | |
|---|---|---|
| 0104591A2 | 4/1984 | European Pat. Off. . |
| WO9408704 | of 0000 | WIPO . |

OTHER PUBLICATIONS

F.W. Zonneveld, Ph.D., Intraoperative CT Scanning in Brain Surgery: Implementation of the Tomoscan M Mobile CT Scanner, Computed Tomography, Philips Medical Systems International B.V., pp. 1–7.

*Primary Examiner*—Terry Lee Melius
*Assistant Examiner*—Robert G. Santos
*Attorney, Agent, or Firm*—Wood, Herron & Evans, L.L.P.

[57] ABSTRACT

An elongated patient support table with a horizontal patient support surface is provided with a radiolucent table extension connected thereto in cantilever fashion for supporting the head and upper torso of a patient. The outer end of the extension has a reduced width compared to the support table to enable extendable movement of the radiolucent extension into a scanning zone of a diagnostic unit such as a CT scanner. The table extension has at its outer end a tool support for supporting and stabilizing medical instruments, and the table extension is tiltable above and below the horizontal. The combination of the support table with the radiolucent table extension supports the patient in a desired posture for an operative procedure both during the scanning and surgical procedures.

28 Claims, 3 Drawing Sheets

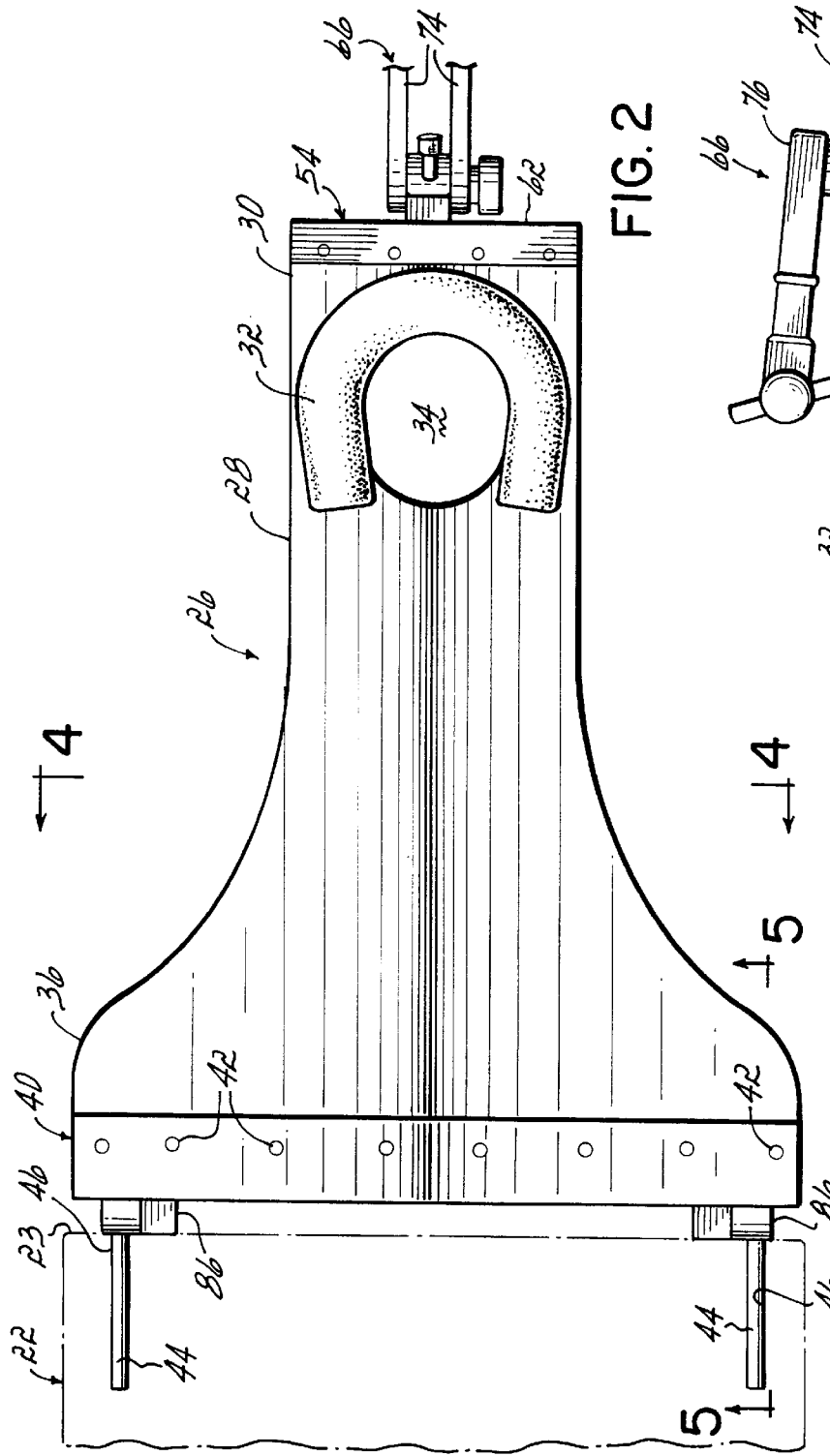
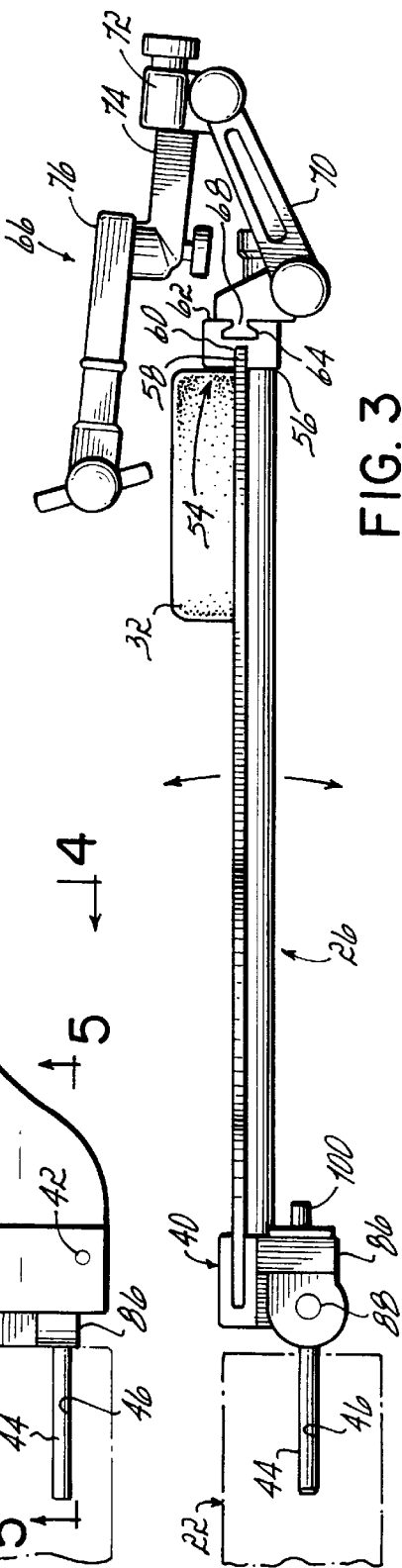

RADIOLUCENT TABLE EXTENSION AND METHOD

FIELD OF THE INVENTION

This invention relates to beds and more particularly, to an improved surgical operating table.

BACKGROUND OF THE INVENTION

With current medical practices, it is common for a patient to undergo a diagnostic scanning procedure, which is normally performed in a separate suite containing the scanning machine and dedicated to scanning procedures. The scanning machine may be a CT, MRI, or other scanning device. Thereafter, the scan data is utilized in a surgical planning process, which conventionally takes place at a location, for example, an office or an operating room. In some surgical procedures, the scanning data is utilized with a system for post processing the scan data acquired during imaging. Further, the imaging system may be located in a surgical suite, and the surgical planning performed before and during surgical procedure utilizing the imaging system and scan data.

During the scanning procedure, the patient must maintain a perfectly still and motionless posture, and while most often, the patient simply lies on a scanning support table, in some situations, the patient may be supported in the desired scanning position with pads, straps or other supports. Further, the support on which the patient rests is normally radiolucent, that is, transparent to the scanning device, so that the support does not compromise the utility of the scanned image. Further, the patient support used for scanning normally translates with respect to the imaging device. Translation of the patient support permits the patient to be moved into the scanning field or zone of the scanning machine.

After the scanning process is completed, often the patient is then moved to an operating room which requires either that the patient walk, or be carried, for example, by transferring the patient from the scanning table to an operating table. Alternatively, as illustrated in U.S. Pat. No. 5,475,884, the patient may be supported on a portable support plate, which is easily moved between the scanning table and the operating table. The scan data is often used in a post processing imaging system for surgical planning purposes both prior to and during surgery. If during or after a surgical process, it is desired to scan a patient again, the patient must be moved from the operating room to the scanning suite, transferred to and from the operating table to the scanning table, and after scanning, transferred back to the operating table and returned to the operating room. The above process is cumbersome, time consuming and potentially risky for the patient.

Some newer scanning machines are substantially reduced in size. Consequently, such scanning machines do not require their own suite or room, but instead, they may be used within the operating suite itself. Thus, in an operating room, the patient may be scanned; the surgical planning performed; an operative procedure executed; and the patient scanned again to determine the current status of the operative procedure. Based on the new scanned images, the operative procedure can be continued and the above process repeated as necessary.

A limitation of the current state-of-the-art is that the posture of the patient during the scanning process is often different from the patient's posture during surgery. If a patient is positioned in one posture on a scanning table during the scanning process, and then is moved to an operating table, that motion of the patient may cause the position of the target to change with respect to the body surface. During surgery, this problem is compounded by tissue shifts attendant to the opening of body cavities, removal of body fluid or tissues and tissue retractions. Thus, while such motion may be small, any motion of the target will reduce or compromise the utility of the preoperative scan data.

The solution to these problems is to scan the patient in the operating room during surgery while the patient is maintained in the surgical posture.

While current scanning tables are radiolucent and provide a translation to move the patient into the scanning machine, such scanning tables do not have the accessories required to attach, support and stabilize surgical instrumentation and to properly support the patient's body in the desired surgical posture. Further, while operating tables contain numerous accessories and couplings to which surgical instrumentation may be attached and supported, most operating tables are not compatible with scanning instrumentation. Thus, as presently known, scanning tables cannot be used as operating tables, and generally, operating tables are inappropriate for use as scanning tables. Therefore, there is a need to provide a patient support or table that not only is compatible for use with a scanning machine, but also provides the necessary tool supports for surgical instruments. Ideally, such a table should permit a patient to be positioned on the table in a posture suitable for a surgical procedure, and further, the table should permit the patient to be scanned in the desired surgical posture. Therefore, the patient is not moved with respect to the patient support during both the scanning and surgical procedures, and hence, a selected target should remain in a fixed and constant position during both the scanning and surgical procedures.

SUMMARY OF THE INVENTION

The present invention provides a radiolucent table extension that permits a patient to be positioned on the table in a posture suitable for a surgical procedure. Further, the table extension permits the patient to be scanned in the desired surgical posture. Therefore, the table extension is especially useful for those procedures in which the patient should remain in a fixed and constant position during both the scanning and surgical procedures.

According to the principles of the present invention and in accordance with the preferred embodiments, a table extension has a first end adapted to be attached to one end of a table. A radiolucent member is designed to support an upper torso and head of a patient with the patient being further supported by an adjacently located surface of the table. A tool support extends along a periphery of the member and is designed to receive and support medical instruments. Therefore, the patient can be supported on the radiolucent table extension in the desired posture. The patient can then be scanned concomitant with a surgical procedure. Further scanning and procedures may be performed if necessary. Thus, the table extension has the advantage of not requiring that the patient be moved with respect to the table extension during both the scanning and surgical procedures.

In one aspect of the invention, a hinge mechanism mechanically couples the member to an operating table, thereby permitting the table extension to be pivoted or rotated with respect to the table. Thus, the patient's head and upper torso may be raised or lowered and supported in any desired position to facilitate the scanning and operative procedures.

In a further aspect of the invention, the tool support extends along the periphery at one end of the table, but in another aspect of the invention, the tool support extends along the periphery including the lateral edges of the table. Thus, a wide variety of surgical instruments may be connected to the table extension to facilitate many different surgical procedures.

These and other objects and advantages of the present invention will become more readily apparent during the following detailed description taken in conjunction with the drawings herein.

BRIEF DESCRIPTION OF THE DRAWINGS

FIG. 2 is a top plan view of the radiolucent table extension of FIG. 1.

FIG. 3 is a side view in elevation of the radiolucent table extension of FIG. 1.

DETAILED DESCRIPTION OF THE INVENTION

Figure 1:
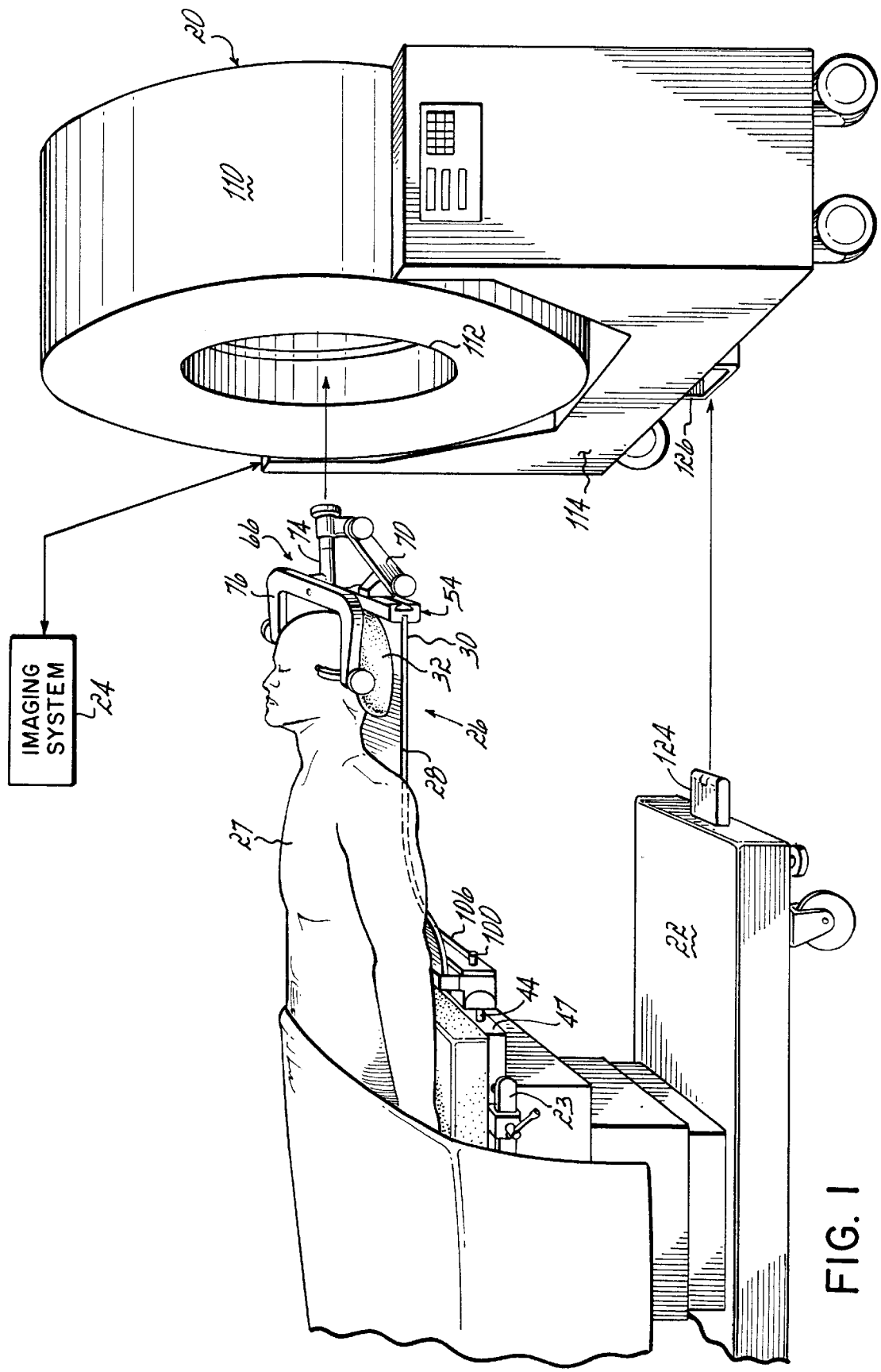
FIG. 1 is a perspective view of a portion of an operating table including a radiolucent table extension in accordance with the principles of the present invention.

Referring to FIG. 1, a portable CT scanning system 20 is located in an operating suite with an operating table 22. The CT scanning system may be either a mobile system such as that commercially available from Analogic of Peabody, Mass. or a stationary scanning system such as that commercially available from General Electric Medical Systems of Milwaukee, Wis. The operating table 22 may be one of many commercially available tables, for example, an operating table commercially available from Amsco of Erie, Pa., MDT Diagnostic Co. of N. Charleston, N.C., or other suppliers. The operating table has a lateral rail 23 extending along each side of the table to which retractors, clamps and other devices may be attached and stably supported. A stereotactic image processing system 24, for example, the MAYFIELD-ACCISS image processing system, commercially available from Ohio Medical Instrument Company, Inc. of Cincinnati, Ohio is responsive to scan data provided by the CT system 20 and provides selected images on a display screen of the scan data along selected planes. To facilitate the use of the operating table 22 with the CT system 20, one end of the operating table is used to support the radiolucent table extension 26.

Figure 4:
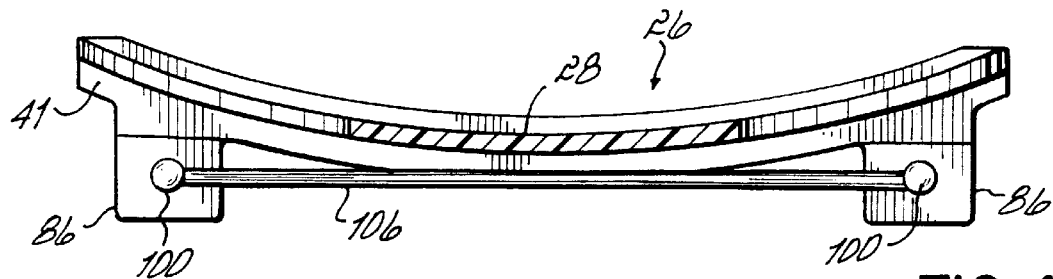
FIG. 4 is a cross-section view taken along the line 4—4 of FIG. 2.

Referring to FIG. 2, the table extension 26 includes a support member or plate 28 made of radiolucent material, for example, wood, carbon graphite, etc., and the table extension 26 has a length to normally support the upper torso and head of a patient 27. The upper torso being defined as the portion of the patient's body above the waist including the head. As shown in FIG. 4, the patient support member 28 has a curved cross-sectional profile and has a laminated construction with a center layer of mahogany between two outer layers of carbon graphite. The curve is normally a circular arc having a relatively large radius, for example, 28 inches. The outer or distal end 30 of the support member 28 includes a headrest 32 that is generally U-shaped and filled with a gel to comfortably and properly support the patient's head. The headrest 32 surrounds an opening 34 within the support member 28. The opening 34 is sized to receive the face of a patient lying on the support member 28 in a prone position. The distal end 30 is narrower than the inner or fixed end 36, and the narrow profile of the distal end 30 of the support plate 28 facilitates positioning the distal end 30 in scanner 20 even if the table or the scanner 20 is tilted. The support member 28, when viewed from the top as shown in FIG. 2, has a profile that flares outward from the distal end 30 to the fixed end 36. The width of the support member 28 at the fixed end 36 is generally greater than the distance between the holes 46 and is normally equal to the width of the operating table 22.

Figure 5:
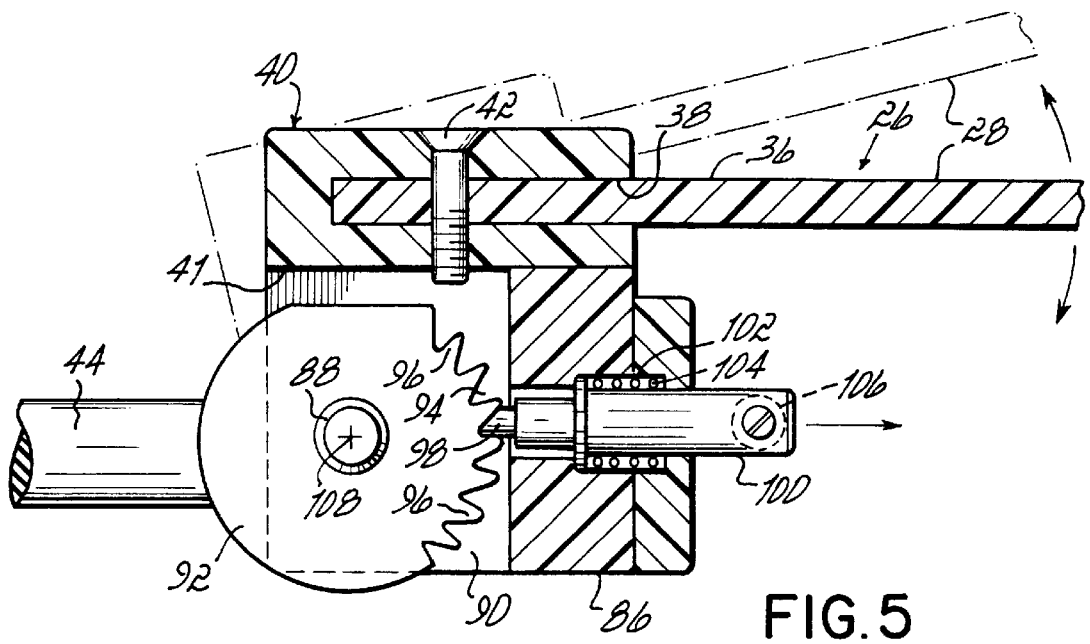
FIG. 5 is a cross-section of view taken along the line 5—5 of FIG. 2.

Referring to FIG. 5, the support member 28 is secured at its fixed end 36 within a slot 38 of an attachment base 40. Fasteners, for example, screws 42 are used to clamp and secure the support plate 28 within the attachment base 40. The attachment base 40 is mechanically linked to support shafts 44, which extend longitudinally from the fixed end of the support base 40 and are sized to fit into holes 46 of the table 22. Thus, the support plate 28 provides an extension of and is cantilevered from the end 23 of the table 22.

Referring to FIGS. 1–3, an instrument or tool support or rail 54 is attached to the periphery of the distal end 30 of the support plate 28. The tool support 54 may be made from a "DELRIN®" acetal polymer material, a polyethersuylfone ("PES") material or a carbon graphite. An inner directed side 56 of the tool support 54 includes a slot 58 for receiving the portion of the periphery 60 of the support plate 28. The support plate 28 may be secured in the slot 58 using fasteners or adhesives or both. The slot 58 is curved with respect to a radius sweeping a vertical plane that is generally perpendicular to and extends across the width of the support plate 28. An outer directed side 62 of the tool support 54 includes a second slot 64 that is generally parallel to a longitudinal center line of the tool support 54. Thus, when viewed from the end of the support plate 28, that is, looking to the left in FIG. 3, the slot 64 will appear generally as a straight slot. The slot 64 permits medical instruments 66, for example, a skull clamp, retractors, clamps, supports, etc., collectively referred to as "tools" herein, to be supported, selectively moved with respect to the distal end 30 of the support plate 28 to desired positions and locked or secured in place. In the illustrated embodiment, the slot 64 has a dovetail shape that matches a mating dovetail on the tool to be mounted and secured to the tool support 54. For example, the tool support 54 may receive one end 68 of a transitional element 70. The other end 72 of the transitional element 70 is rotatably coupled to a swivel adapter 74. The swivel adapter, in turn, is coupled to a skull clamp 76. The skull clamp 76 is normally manufactured from radiolucent materials, for example, as described in U.S. Pat. No. 5,276,927 issued to the assignee of the present invention.

As shown in FIG. 3, the support plate 28 is often used in a generally horizontal position such that the top of the operating table 22 is generally in line with the support plate 28. However, numerous surgical procedures require that the support plate 28 be tilted or pivoted up or down with respect to the end 25 of the table 22. The tilting or pivoting of the support plate 28 is accomplished by the mechanism illustrated in FIG. 5. The attachment base 40 includes a pair of housings 86 connected to a lower surface 41 at a location near the ends of the attachment base 40 (FIG. 4). The attachment base 40 and housings 86 may be cast or made from aluminum. The support shafts 44 are rigidly connected at one end to respective cross-shafts 88 that are rotatably mounted within the lateral side walls 90 of the housings 86. The cross-shafts 88 extend through brass bushings (not shown) mounted in the lateral side walls 90 and function as pivot pin in a hinge. The support shafts 44 function as fixed hinge members, and the housings function as movable hinge members. A ratchet wheel 92 is fixed at the center of each of the cross-shafts 88, and each ratchet wheel has notches 94 between teeth 96. The support shafts 44, cross-shafts 88, and ratchet wheels 92 are normally made from stainless steel.

Pawls 98 are shaped to mate with and fit into the notches 94 of respective ratchet wheels 92. Each pawl 98 is mounted on the end of a release shaft 100 that extends through a bore 102 of a respective housing 86. With the pawls 98 in the position illustrated in FIG. 5, they function to securely support their respective housings 86 and the support plate 28 in a generally horizontal position. A spring 104 provides a bias to forcibly maintain the pawls 98 within the slots 94. The pawls 98 and release shafts 100 are normally made of stainless steel.

As shown in FIG. 4, a release shaft or bar 106, normally made of aluminum or stainless steel, extends between the shafts 100 and the housings 86. By pulling on the bar 106, the shafts 100 move to the right as viewed in FIG. 5; and the pawls 98 are pulled out of engagement with respective ratchet notches 94. Once the pawls 98 are disengaged from the notches 94, the support plate 28, attachment base 40, and housings 86 are freely rotatable relative to respective stationary ratchet wheels 92, cross-shafts 88 and support shafts 44. Thus, the support plate 28 may be pivoted with respect to an axis of rotation 108 in the generally clockwise or counter-clockwise direction until the support plate 28 is at its desired angular position as shown in phantom in FIG. 5. Normally, the support plate 28 may be pivoted approximately 60° above and below its illustrated horizontal position. When the bar 106 is released, the springs 104 push their respective pawls 98 into the closest ratchet notches 94, thereby securing the support plate with the desired angle or tilt.

In use, referring to FIG. 1, the scanning system 20 and operating table 22 are brought into a surgical suite. The scanning system 20 has a toroid shape scanning element 110 with a central opening 112 with which the portion of the patient to be scanned is axially aligned. The scanning element 110 further has the capability of rotating or tilting within its base 114 with respect to a diametric horizontal axis. The distal end 30 of the support plate 28 is narrowed so that it can extend into the opening 112 without interference. If necessary, the head section (not shown) of the table 22 is removed therefrom, and the radiolucent table extension 26 is mounted to the table by inserting the support bars 44 into mating bores 46 on the end surface 47 of the table 22. The patient 116 is then positioned on the table in a posture suitable for a surgical procedure. The length of the support plate 28 is sized such that the patient's upper torso and head are accessible for scanning and surgical procedures. The portion of the patient's anatomy on which the surgical procedure is to be performed may be stabilized by various clamps and restraining devices, for example, the skull clamp 76. Further, the support plate 28 or the scanning element 110 may be tilted so that the desired posture and/or scanning plane is achieved.

When the desired surgical posture is achieved, normally the patient will have already been scanned; and the surgical planning and procedure can be performed. A portion of the radiolucent table extension 26 is then moved into the opening 112. The extent to which the extension 26 is moved into the opening 112 depends on what portion of the head or upper torso is to be scanned. The initial alignment of the table extension may be determined by visual inspection; and thereafter, a scan made to determine exactly whether and to what extent the table extension may be out of alignment. Alternatively, the scanner may be equipped with LED's or other sources of light providing beams of light with which the table extension can be aligned. In another embodiment, the table 22 may have an alignment tab 124 (FIG. 1) which is moved into an alignment slot 126 on the scanner 110. When the tab 124 is properly seated in the slot 126, the table is properly aligned with the scanner 110. The scanning process is executed by the scanning machine moving the scanning element 110 incrementally in an axial direction and with each increment, a scan is taken. Thereafter, the patient is removed from the scanning element 110, either by moving the scanning machine 20 or the operating table 22. The scan data is then used in association with the imaging systems 24 to plan the surgical procedure. The surgical procedure is then performed, and thereafter, the patient may be moved back into the scanning machine 20, and the scanning process repeated. The scanning and imaging system may be used to gauge the effectiveness of the surgical procedure; and if necessary, further procedures performed. The above process may be executed any number of times with the patient remaining in the desired position on the same patient support.

Thus, the above-described operating table and radiolucent table extension has a significant advantage of not only being able to support a patient during a scanning process, but also support the patient in the identical posture during a surgical procedure. The radiolucent table extension permits an operating table that is normally nonradiolucent and inappropriate for scanning purposes to be used with a scanning machine. Further, the table extension may be tilted to accommodate different desired surgical postures and is sized and shaped to readily fit within the opening of a scanning element, whether in a horizontal or tilted position. Further, not only does the table position permit simultaneous scanning and operative procedures on the upper torso and head of a patient, but the radiolucent table extension 26 readily supports the patient in a prone, or supine position.

Figure 6:
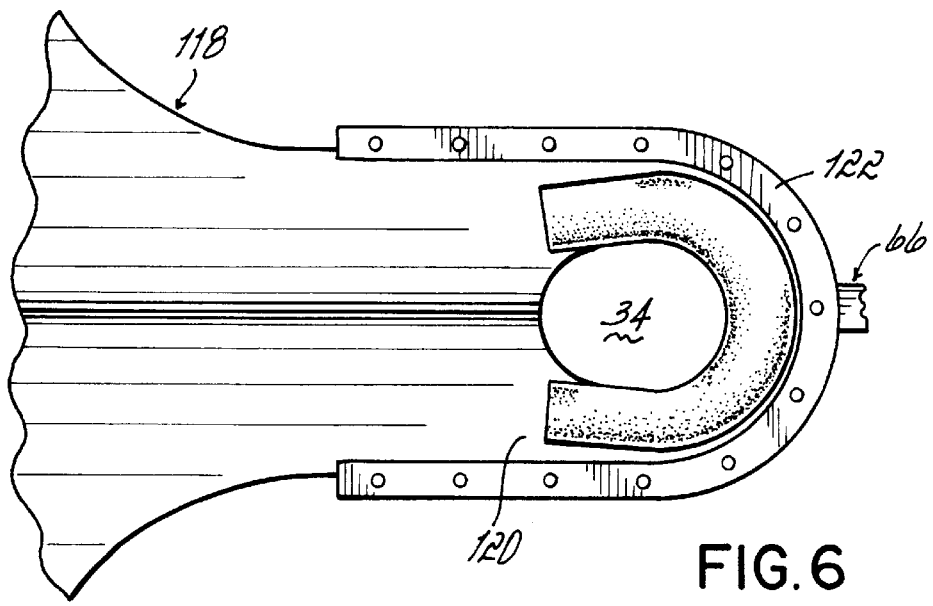
FIG. 6 is a top plan view of an alternative embodiment of the radiolucent table extension in accordance with the principles of the present invention.

Referring to FIG. 6, an alternative embodiment of the support plate 118 has an distal end 120 that is curved to generally follow the profile of the headrest 32. Further a tool support 122 extends along the periphery of the support plate 118 to a location at which the width of the support plate 118 begins to flare outwardly toward the width of the fixed end 32. Other than its length, the construction and function of the tool support 122 is substantially identical to the tool support 54 described earlier.

While the invention has been illustrated by the description of one embodiment and while the embodiment has been described in considerable detail, there is no intention to restrict nor in any way limit the scope of the appended claims to such detail. Additional advantages and modifications will readily appear to those who are skilled in the art. For example, the support plate 28 may be made of other radiolucent materials and may or may not have a laminated construction. Further, when viewed in a cross-section taken across its width as shown in FIG. 4, the support plate 28 has a curvature; however, the support plate 28 may also be constructed to be flat without such a curvature. Further, while the radiolucent table extension is particularly useful with nonradiolucent operating tables, it may also be used with radiolucent operating tables.

The tool support 54 has been described as an edge strip with a slot 64 having a dovetail shape for receiving and supporting tools; however, as will be appreciated, other configurations of the tool support are anticipated by the invention. For example, the slot 64 may have other shapes. Further, the slot 64 may be replaced by round, square or other shaped holes or coupling elements which are shaped to receive mating elements on tools, thereby supporting and holding the respective tools in a desired position. In addition, the tool support 54 may be a strip extending along the edge of the periphery of the plate 28 without the slot 64 but providing a hard surface for clamping purposes, for example, for using C-clamps to secure tools to the strip. While the tool support 54 is described and illustrated as having a slot 58 for receiving an edge of the plate 28, the tool support 54 can be attached to the plate 28 in other ways. For example, the slot 54 may be on the upper or lower surfaces of the plate 28, or the tool support 54 can be attached to the upper or lower surfaces, or the edge, of the plate 28. In addition, even though the tool support 54 has been described as being made from a radiolucent material, under some circumstances, for example, if the tool support is outside the scan field, the tool support 54 may be made of a nonradiolucent material, for example, metal.

As will be appreciated, the horseshoe-shaped gel filled headrest 32 illustrated and described may have other embodiments. For example, the headrest may be circular or another shape, may be filled with a different material, or may be thicker so that the patient's head is supported fully above the upper surface of the support plate 28. Further, the opening 34 may have other configurations. For example, the opening 34 may be replaced by, or supplemented by, one or a plurality of holes of any shape for various purposes, for example, ventilating the patient, access for tubes and other equipment, drainage, or openings through which the patient can see or the patient's eyes can be seen. As will be appreciated, separate inserts or built-in hole covers may be used to fill or cap the holes when they are not being used.

As will be appreciated, the aligning tab 124 may be located on the scanner 20, and the slot 126 located on the table 22. In addition, other alignment devices and procedures may be used. For example, the scanner 20 may have a built-in aligning system or the imaging system may be used to align the table 22 to the scanner 20.

Therefore, the invention in its broadest aspects is not limited to the specific details shown and described. Consequently, departures may be made from the details described herein without departing from the spirit and scope of the claims which follow.

What is claimed is:

1. A table extension attachable to a table for use with a scanning machine comprising:
    a radiolucent member having:
        a first end adapted to be attached to one end of a table;
        opposed lateral edges;
        a distal end; and
        a patient supporting surface extending between the lateral edges and the first and distal ends of the radiolucent member, the patient supporting surface providing subjacent contact and support for an upper torso and head of a patient; and
    a radiolucent tool support extending along a portion of a periphery of the radiolucent member, the tool support adapted to receive and support medical instruments.

2. The table extension of claim 1 wherein the member has a distal end having a width permitting movement of the distal end of the member into a scanning zone of the scanning machine.

3. The table extension of claim 2 wherein the distal end of the member has a width less than a width of the first end of the member.

4. The table extension of claim 1 further comprising a base connected to the first end of the member and adapted to removably mount the member to the table.

5. The table extension of claim 4 further including a mechanism operatively connected to the base for permitting the member to be selectively pivoted with respect to the first end of the member.

6. The table extension of claim 5 wherein the mechanism supports the member at a selected angle.

7. The table extension of claim 6 wherein the mechanism includes a locking element for mechanically locking the member at the selected angle.

8. The table extension of claim 7 wherein the mechanism includes a pivot joint permitting the member to be pivoted with respect to an axis of rotation extending in a direction coextensive with the width of the member.

9. The table extension of claim 2 further comprising a headrest secured to the member.

10. The table extension of claim 2 wherein the member further includes an opening positioned adjacent a head of the patient.

11. The table extension of claim 9 wherein the headrest has a perimeter and the member further includes an opening within the perimeter of the headrest, the opening adapted to receive a face of the patient lying in a prone position.

12. The table extension of claim 1 wherein the member has contoured side edges extending between the first and distal ends.

13. The table extension of claim 1 wherein the member has a contoured upper surface for supporting an upper torso of the patient.

14. The table extension of claim 1 wherein the member is adapted to be cantilevered from the one end of the table.

15. A table extension attachable to a table for use with a scanning machine comprising:
    a radiolucent member having:
        a first end adapted to be attached to one end of a table;
        opposed lateral edges; and
        a distal end; and
        a patient supporting surface extending between the lateral edges and the first and distal ends of the radiolucent member, the patient supporting surface providing cantilevered subjacent contact and support for an upper torso and head of a patient; and
        the distal end being sized to be received within a scanning zone of a scanning device; and
    a radiolucent tool support extending along a portion of a periphery of the radiolucent member, the tool support adapted to receive and support medical instruments.

16. The table extension of claim 15 wherein the distal end has a width narrower than a width of the first end of the member.

17. A table extension attachable to a table for use with a scanning machine comprising:
    a radiolucent member having:
        a first end adapted to be attached to one end of a table;
        opposed lateral edges;
        a distal end;
        a patient supporting surface extending between the lateral edges and the first and distal ends of the radiolucent member, the patient supporting surface providing subjacent contact and support for an upper torso and head of a patient, and the patient supporting surface having an opening adapted to be positioned adjacent the head of the patient; and a radiolucent tool support extending along a portion of a periphery of the radiolucent member, the tool support adapted to receive and support medical instruments.

18. An apparatus for supporting a patient during a scanning process being performed by a scanner having a scanning zone comprising:
an operating table having:
first and second ends;
a support surface extending between the ends and adapted to support a patient; and
lateral rails adapted to receive and support medical instruments;
a radiolucent patient support mounted on the first end of the operating table, the radiolucent patient support having:
an inner end adjacent the first end of the operating table;
lateral edges;
a distal end;
a patient supporting surface extending between the lateral edges and the inner and distal ends of the radiolucent table extension and providing subjacent contact and support for an upper torso of a patient; and
a radiolucent tool support extending along a portion of a periphery of the radiolucent patient support, the tool support adapted to receive and support medical instruments.

19. An apparatus for supporting a patient during a scanning process being performed by a scanner having a scanning zone comprising:
an operating table having a support surface adapted to support a patient, the table having first and second ends for supporting head and foot ends of a patient, respectively; and
a radiolucent table extension removably mounted at the first end of the operating table, the radiolucent table extension having:
an inner end adjacent the first end of the operating table;
lateral edges;
a distal end;
a patient supporting surface extending between the lateral edges and the inner and distal ends and providing subjacent contact and support for an upper torso of a patient; and
a radiolucent tool support extending along a portion of a periphery of the distal end of the radiolucent table extension, the tool support adapted to receive and support medical instruments.

20. A method of handling a patient during successive scanning and operative procedures comprising:
removably attaching a radiolucent table extension having a radiolucent tool support to one end of an operating table, the table extension providing subjacent contact and support for a head and upper torso of a patient;
placing a patient on an upper surface of the operating table and the radiolucent table extension;
positioning the patient in a desired posture on the radiolucent table extension;
performing an operative procedure on the patient with the patient in the desired posture;
putting the radiolucent table extension and its radiolucent tool support into juxtaposition with the scanning machine by moving the operating table and table extension relative to the scanning machine to locate the table extension within a toroidal shaped scanning zone of the scanning machine; and
performing a scanning procedure on the patient with the patient in the desired posture.

21. The method of claim 20 wherein before performing an operative procedure, the method further comprises:
putting the radiolucent table extension with its radiolucent tool support into juxtaposition with the scanning machine by moving the operating table and table extension relative to the scanning machine to locate the table extension within a toroidal shaped scanning zone of the scanning machine; and
performing a scanning procedure on the patient with the patient in the desired posture.

22. The method of claim 20 wherein after performing a scanning procedure, the method further comprises performing another operative procedure on the patient.

23. The method of claim 20 further comprising providing a radiolucent table extension having a tool support extending along a periphery of the table extension.

24. The method of claim 20 further comprising providing a table extension shaped to fit within a scanning zone of the scanning machine.

25. The method of claim 20 further comprising the steps of:
tilting the radiolucent table extension with respect to the table; and
placing the patient in the desired posture on a tilted radiolucent extension.

26. The method of claim 20 and further comprising:
storing, in an imaging system, operatively connected to the scanning machine, images representative of the patient and obtained during performance of the scanning procedure.

27. In combination, the invention comprising:
a portable scanning machine having a toroidal shaped scanning zone and adapted to take scans in the scanning zone;
an imaging system operatively connected to the scanning machine and adapted to store images representative of scans of the scanning zone taken by the scanning machine;
a patient table having an upper support surface, the patient table and upper support surface including a radiolucent table extension adapted to support a head and upper torso of a patient residing in a prone position on the upper support surface, the radiolucent table extension being sized to be received within the scanning zone, the patient table and the radiolucent table extension being movable relative to the scanning machine to locate the radiolucent table extension within the scanning zone, and the radiolucent table extension including at least one of the following:
a radiolucent headrest located inboard of an outer edge of the table extension and adapted to stabilize the head of the patient; and
a radiolucent tool support located along the edge of the table extension and holding a radiolucent head clamp adapted to securely hold the head of the patient in a fixed position relative to the table extension, thereby to assure the accuracy of scans taken of the patient by the scanning machine and subsequently stored in the imaging system.

28. A table extension attachable to a table for use with a scanning machine comprising:

a radiolucent member having:
- a first end adapted to be attached to one end of a table;
- opposed lateral edges;
- a distal end; and
- a patient supporting surface having a periphery formed by the lateral edges and the first and distal ends of the radiolucent member, the patient supporting surface providing subjacent contact and support for an upper torso of a patient; and a radiolucent tool support extending along a portion of the periphery of the patient supporting surface, the tool support adapted to receive and support medical instruments.

* * * * *